Figure 1:
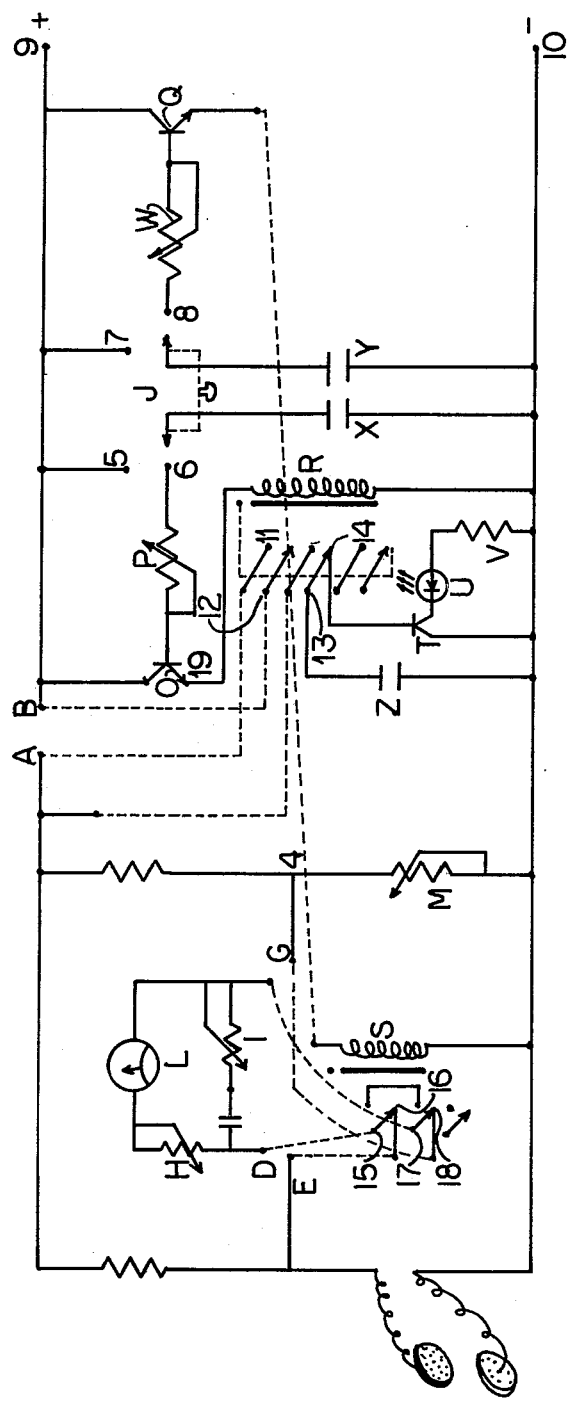

United States Patent [19]

Bacchelli

[11] 4,109,645
[45] Aug. 29, 1978

[54] DEVELOPMENT OF INSTRUMENTS MEASURING BODY RESISTANCE TO ION AND IONOPHORESIS APPLICATIONS

[76] Inventor: Sancio Bacchelli, 12, via Indipendenza, Bologna, Italy

[21] Appl. No.: 687,333

[22] Filed: May 17, 1976

[30] Foreign Application Priority Data

May 23, 1975 [IT] Italy .................................. 3420 A/75
Dec. 11, 1975 [IT] Italy .................................. 3614 A/75

[51] Int. Cl.² .............................................. A61B 5/05
[52] U.S. Cl. .............................................. 128/2.1 Z
[58] Field of Search ............... 128/2.1 Z, 2.1 R, 172.1

[56] References Cited

U.S. PATENT DOCUMENTS

| 3,468,302 | 9/1969 | Cowell | 128/2.1 R |
| 3,866,600 | 2/1975 | Rey | 128/2.1 R |
| 3,894,532 | 7/1975 | Morey | 128/2.1 Z |
| 3,901,214 | 8/1975 | Taaffe | 128/2.1 Z |

*Primary Examiner*—Robert W. Michell
*Assistant Examiner*—Lee S. Cohen
*Attorney, Agent, or Firm*—Martin A. Farber

[57] ABSTRACT

An instrument for measuring body resistance to ion and ionophoresis applications comprising a reading circuit for providing a reading of body resistance values after an established period during which the resistance values become stable, and a principle circuit including two transistors for initially obstructing current to a bridge and two condensors for actuating the two transistors, the condensors providing a discharge time equal to the time necessary for the body resistance values to become stable. Two relays are activated by the current circulating in the transistors and close the reading circuit.

4 Claims, 1 Drawing Figure

DEVELOPMENT OF INSTRUMENTS MEASURING BODY RESISTANCE TO ION AND IONOPHORESIS APPLICATIONS

This invention concerns a development in instruments measuring body resistance to ion and ionophoresis applications.

It is well known, in fact, that human tissue resistance varies from one person to another: for this reason, an instrument capable of measuring such resistance has been developed and this is the subject of the present inventions. Subsequent tests have demonstrated that the above mentioned instruments were insufficient, owing to the fact that the resistance offered by tissues appears not to be constant for each person, but varies according to both the applied voltage and the time of the application. After carrying out several measurements on different people under different conditions of application, it has been possible to determine some general features which can be summed up as follows: the resistance offered by tissues to the passage of current decreases when the applied voltage increases and after a certain period of time this resistance goes down to values far lower than the initial ones. Such a behaviour is connected to the vasodilator effect of the galvanic current, even if its magnitude cannot be explained.

It has also been noted that from the quantitative point of view, the phenomenon is nearly constant for all people, while the reaction time varies considerably from one person to another, resulting in greater scalding danger for some people.

The logical explanation for the above mentioned phenomenon can be given by Joule's and Ohm's law by which tissues tend to offer the weakest resistance possible, because, when the resistance R decreases, the power W to be dissipated in heat decreases too, according to the law $W = RI^2$. Now, as the ionizing product conveyance through galvanic currents depends only on the current intensity I and on the time of application, the galvanic current generating instrument for ionophoresis must necessarily have a current regulation.

All this is because, according to the $W = VI$ and $W = RI^2$ laws, it is apparent that, keeping I constant and decreasing R, in order to keep the power W constant, it will be necessary to decrease the voltage V, hence the ion passage and its speed wll remain constant, thus avoiding scalding danger. But if voltage regulated generators are used, greater danger would be present because, when R varies at a constant voltage V, the current intensity I quadratically increases according to $W = RI^2$ by the effect of which there will be an increase in power W dissipated as heat, with scalding possibility and an excessive increase in penetration speed. In our present technical situation the determination of the current intensity of application is based only on patient's sensation of pain the inevitable and imaginable consequences of which are connected to the major or minor patient's sensitiveness.

This invention has as an object to develop an instrument capable of determining the exact intensity of current to be applied in each case.

For this purpose, our measuring instrument is provided with electrodes connected to a Wheatstone bridge fed by the same voltage of the galvanic current generator, upstream of the current generator, making the reading possible after an established period of time during which time the tissue resistance tends to become stable (in general after about 10 seconds). In this way it will be possible to avoid the regulation of current intensity on transitory values and thus on non-defined values for ionophoresis application.

Additional purposes and advantages will be apparent from the following specification and from the accompanying drawings which illustrates in an explanatory and schematic way a possibility of realisation of this invention.

With reference to the drawing,

FIG. 1 shows schematic electric circuit of the measuring instrument, where the Wheatstone bridge or potentiometer W is the base element for measuring body resistance — according to Italian application 3420 A/75 — and the other circuits form the regulation element.

The circuit input is applied at the input points 9 and 10 with a voltage which may vary from 12 v to 40 v, according to the type of feed.

By manually pushing the knob of the double switch J, the condensers X and Y are charged through the contact points 5 and 7; by releasing the knob of switch J, contact is attained between the electrolytic condensers X and Y, through the contacts 6 and 8, and the transistor bases O and Q, through semiportable potentiometers P and W; the function of these potentiometers is to regulate the discharging time and intensity of the condensers X and Y, which come into conduction exciting the relays R and S.

The contacts A and B of the relay R give current to the bridge through the corresponding points 11 and 12, while the contacts 13 and 14 will charge the condenser Z. The contacts D and G of the relay S short-circuit the instrument L, which is equipped with condenser, bringing about its zero setting.

The potentiometer W is regulated for a discharging time of the condenser Y of about 10 seconds, after which, as the condenser Y is discharged, the transistor base Q will not require any current, by effect of which the transistor Q will no longer conduct current, dropping out the relay S; in this way through contact points 15 and 16, 17 and 18, the instrument L will be connected with the points E and G of the bridge: the instrument L will show the bridge unbalance.

The purpose of the condenser is to keep the instrument in a reading position for a few seconds, also after the circuit drop out.

Five seconds after the dropping out of relay S, the condenser X also discharges, and this, since it no longer polarizes the transistor base O, blocks the circulating current by the effect of which the relay R drops out. When the relay R drops out, it turns off the current from the bridge through the contacts 11 and 12; the condenser Z is connected to the transistor base T which comes into conduction for a few seconds (equal to the condenser Z discharging time) showing the operator the reading time through the U luminous LED which lights up. After reading it is possible immediately to effect the same operation in other parts of the body.

The function of the semi-portable resistances H and I is to calibrate the instrument during its construction to the desired reading, given by calibration graphics. The potentiometer M is calibrated only once during its construction in order to have a good reading.

It a simplification of the instrument is desired, it is possible to remove the luminous indicator U and hence also the condenser Z, the transistor T and the limiting resistance V.

Further in this way, it is possible to also remove the relay R, merely by connecting the emitter 19 of the transistor to the point A, keeping all the other components unchanged, without losing any reading accuracy.

This invention, is illustrated and described in a schematic and explanatory way, and not in a limiting sense.

I claim:

1. An instrument for measuring body resistance to ion and ionophoresis applications, comprising
    a reading circuit means including a reading meter for providing a reading of resistance values after an established period during which the resistance values become stable,
    a principal circuit including electrodes adapted to be positioned on the body, a bridge means operatively connected to said electrodes and to said reading circuit means for measuring body resistance derived from said electrodes and for supplying the measurement to said reading circuit means and two transistor means for initially obstructing current to said bridge means,
    two condenser means releaseably operatively connected to said two transistor means, respectively, through said bridge means, for discharging and activating said two transistor means, said two condenser means for cooperating with said bridge means for providing a discharging time thereof equal to a time necessary for the body resistance values to become stable,
    two relay means being operatively connected to said two transistor means, respectively, and one of said two relay means being operatively connected to said reading circuit means, said relay means being activated by current circulating in said two transistor means, respectively, and said one of said relay means for closing said reading circuit means when one of said two transistor means is activated during the discharging time of one of said two condenser means and for connecting said reading circuit means to said bridge means after said one condenser means discharges.

2. The instrument as set forth in claim 1 further comprising
    two voltage supply lines,
    said principal circuit includes a secondary circuit, the latter includes,
    a transistor,
    a condenser connected to the other relay means and selectively via said other relay means to said voltage supply lines when said other relay means is activated during discharging of the other of said condenser means, and across said transistor after said other condenser means discharges and said other relay means is deactivated, respectively,
    a resistor connected to one of said supply lines,
    a warning light means operatively connected to and between said transistor and said resistor for lighting up and for showing the correct moment to obtain an accurate reading of the body resistance values.

3. The instrument as set forth in claim 2 wherein
    said bridge means comrises a first potentiometer and a second potentiometer, each potentiometer is connected to one of said transistor means,
    a double switch means selectively connected between said first and second potentiometers and to one of said supply lines, respectively, and permanently connected to said two condenser means for connecting said condenser means directly between said voltage supply lines in a first position thereof for charging of said condenser means, and for connecting said condenser means to said first and second potentiometers, respectively, in a second position thereof for the discharging of said condenser means, and
    said two transistor means each have a base connected to one of said potentiometers, respectively,
    said one relay means is connected to one of said transistor means and to said reading circuit means, and said other relay means is connected to the other of said transistor means and to said secondary circuit,
    said other relay means for providing current to said bridge means via said supply lines by activation of said other relay means during discharging of said other condenser means.

4. The instrument as set forth in claim 3 wherein
    said reading circuit means includes,
    a first variable resistor connected to said reading meter, and
    another condenser and a second variable resistor connected in series to each other and in parallel across said first variable resistor and said reading meter,
    another resistor and an adjustable resistor connected in series and to and between said voltage supply lines, a contact connected between said another resistor and said adjustable resistor, said contact connected to said one relay means for selective connection to said reading circuit means via said one relay means.

* * * * *